Figure 1:
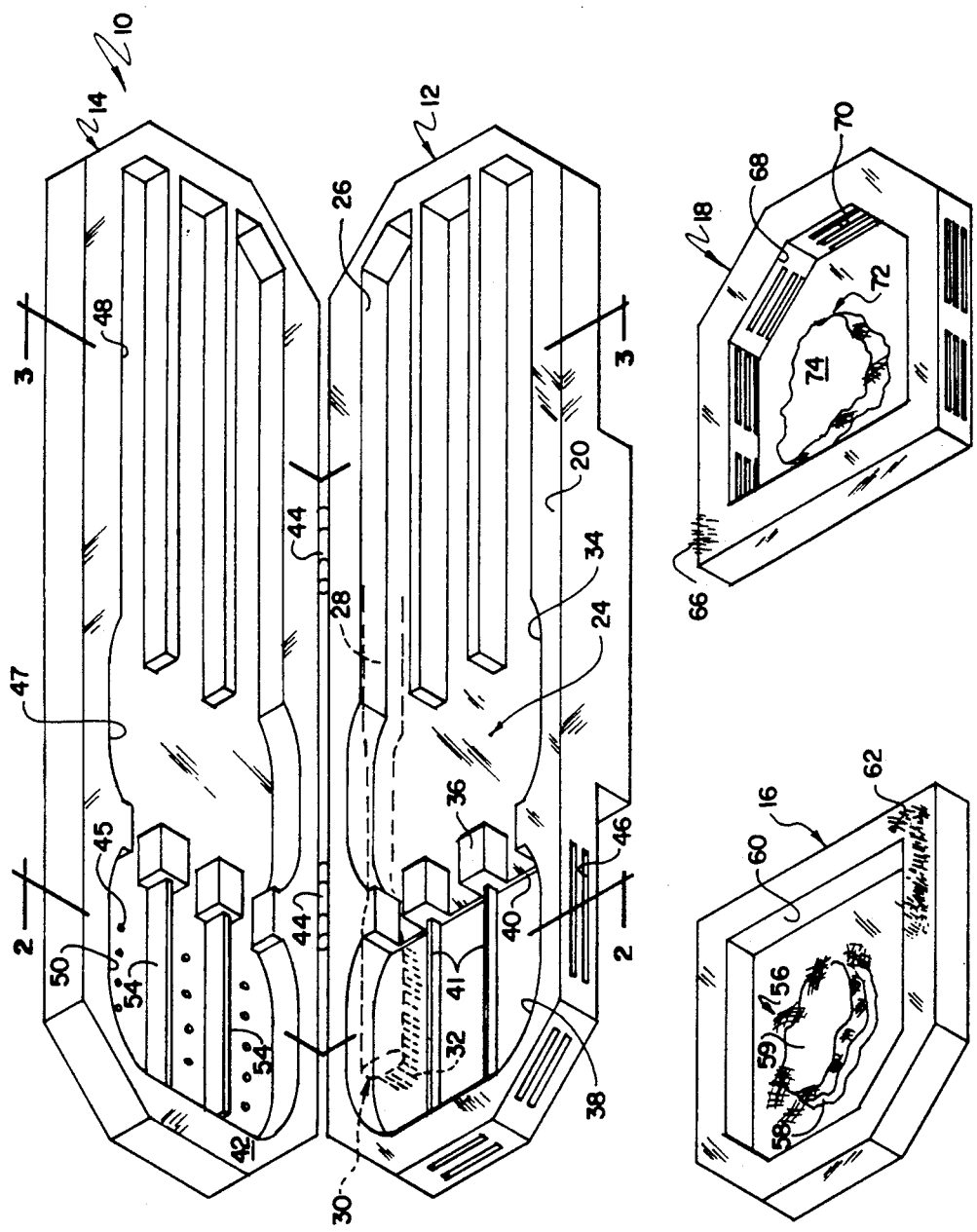

United States Patent [19]

Gonzalez

[11] Patent Number: 5,295,575

[45] Date of Patent: Mar. 22, 1994

[54] TOOTHBRUSH HOLDER AND ROOM ODORIZER

[76] Inventor: Santos O. Gonzalez, 1223-A Chris Cir., Edinburg, Tex. 78539

[21] Appl. No.: 78,450

[22] Filed: May 20, 1993

[51] Int. Cl.⁵ .............................................. A45D 44/18
[52] U.S. Cl. .................................... 206/204; 206/216; 206/362.2
[58] Field of Search .................... 206/204, 209, 209.1, 206/362.1, 362, 361, 362.2, 362.3, 15.2, 15.3, 0.5, 581, 216

[56] References Cited

U.S. PATENT DOCUMENTS

| | | | |
|---|---|---|---|
| 1,041,315 | 10/1912 | Marx | 206/204 |
| 1,625,202 | 4/1927 | Gindick | 206/209.1 |
| 1,954,085 | 4/1934 | McMillan | 206/362.1 |
| 2,642,331 | 6/1953 | Sprinkle | 206/362.1 X |
| 3,741,378 | 6/1973 | Parker | 206/209 |
| 4,175,659 | 11/1979 | Horian et al. | 206/362 X |
| 4,890,732 | 1/1990 | Shackelford | 206/362.1 |

Primary Examiner—Paul T. Sewell
Assistant Examiner—Jacob K. Ackun, Jr.
Attorney, Agent, or Firm—G. Turner Moller

[57] ABSTRACT

A toothbrush holder includes a base having a plurality of indentations for receiving a plurality of toothbrushes. The base includes a series of parallel openings receiving the bristles of the toothbrushes. The openings are exposed on the bottom of the base and communicate with a closure having an absorptive fiber mass and a desiccant therein. A second container is attached to the bottom of the base to make the toothbrush holder symmetrical and to provide an odorant material.

11 Claims, 2 Drawing Sheets

TOOTHBRUSH HOLDER AND ROOM ODORIZER

This invention relates to a toothbrush holder and more particularly to a toothbrush holder for drying and sanitizing toothbrushes. The toothbrush holder of this invention comprises a container for storing toothbrushes and uses a disposable filter which dries and sanitizes the toothbrushes and the inside of the container. The toothbrush holder also incorporates a disposable odorizer.

Toothbrush holders of the prior art fall into two basic types. The first type suspends a toothbrush in the open air and is typically attached to a bathroom wall or fixture. The second type encloses a toothbrush inside a container which isolates the toothbrush from the open air.

One problem with toothbrush holders suspended in the open air is that the toothbrushes are too vulnerable to contamination by airborne bacteria or viruses. One problem with the enclosed toothbrush holders of the prior art is that chemicals have to be placed in the container to dry and sanitize the toothbrushes. These chemicals are not convenient to use and are often difficult to obtain, are poisonous and are therefore not desirable to have in a home with small children. Other holders of the second type require the use of electricity to dry and sanitize toothbrushes and are therefore expensive, cumbersome and incapable of being used as a traveling case. The prior art toothbrush holders are, almost without exception, either structurally complex, difficult to manufacture, operate or maintain, bulky, aesthetically outdated or some combination thereof. Typical prior art toothbrush holders are found in U.S. Pat. Nos. 941,200; 1,212,335; 1,951,585; 2,280,431; 2,468,733; 3,367,610; 3,741,378; 3,794,181 and 3,884,635.

This invention overcomes these disadvantages of the prior art and provides a novel sanitary toothbrush holder for separately holding a plurality of toothbrushes. The toothbrush holder of this invention protects the toothbrushes from dust and airborne contaminants and provides a drying and sanitizing environment.

This invention comprises a holder for toothbrushes comprising an elongate handle and a bristle section including a base having a plurality of indentations therein open to a first side of the base for receiving a plurality of toothbrushes and a plurality of openings therethrough communicating with a second side of the base, the handles being receivable in the indentations and the bristle section being receivable in the openings, a lid and means movably mounting the lid on the base for closing the first side of the base and closure means for the second side of the base and means detachably connecting the closure means on the base for closing the second side of the base, the closure means including a desiccant and a mass of fibers aligned with the openings, the fibers being between the desiccant and the openings.

It is an object of this invention to provide an improved toothbrush holder.

Another object of this invention is to provide a toothbrush holder having means for drying and sanitizing toothbrushes in a simple and expeditious manner.

Another object of this invention is to provide a toothbrush holder having means for odorizing the surrounding environment.

These and other objects of this invention will become more fully apparent as this description proceeds, reference being made to the accompanying drawings and appended claims.

IN THE DRAWINGS

Figure 2:
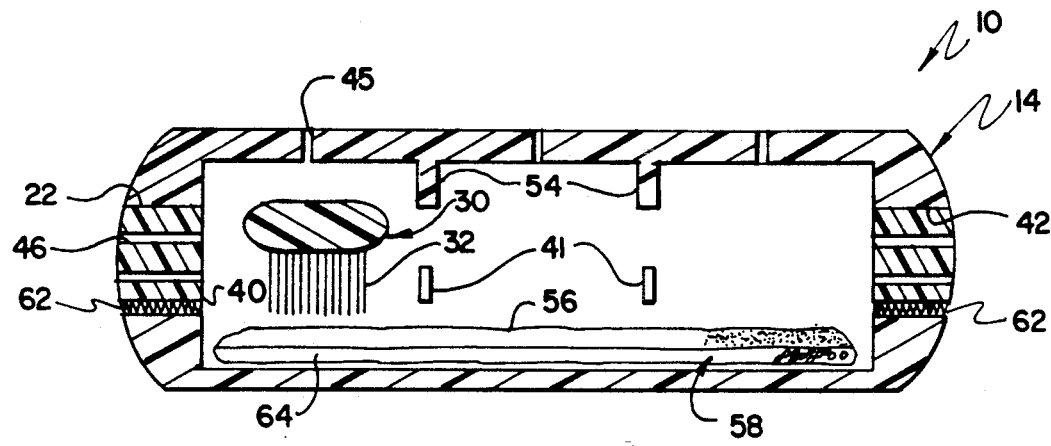
Figure 3:
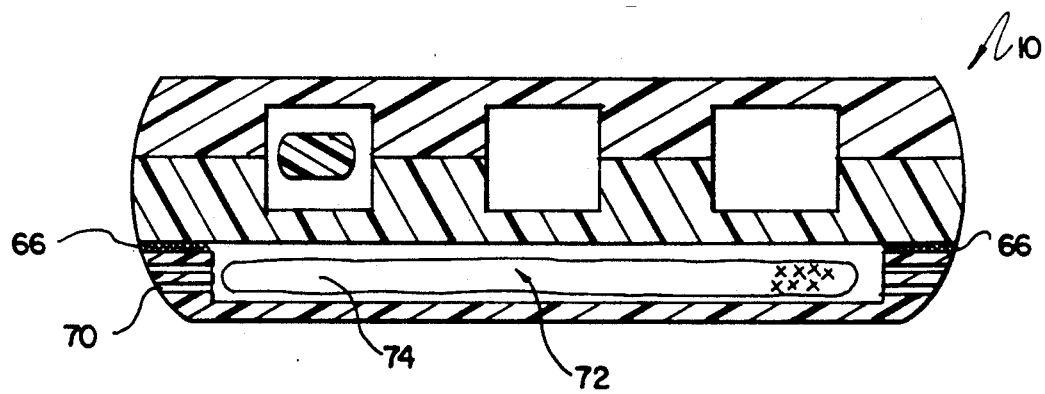

FIG. 1 is an exploded view of a toothbrush holder of this invention;

FIG. 2 is an enlarged cross-sectional view of the toothbrush holder of FIG. 1, taken substantially along line 2—2 thereof, as viewed in the direction indicated by the arrows, illustrating the holder in a closed position; and FIG. 3 is an enlarged cross-sectional view of the toothbrush holder of FIG. 1, taken substantially along line 3—3 thereof, as viewed in the direction indicated by the arrows, illustrating the holder in a closed position.

Referring to FIGS. 1-3, a toothbrush holder 10 of this invention comprises a base 12, a lid 14 closing one side of the base 12, a first closure 16 closing one end of the opposite side of the base 12 and a second closure 18 closing a second end of the opposite side of the base 12.

The base 12 is made of any suitable material, such as injection molded plastic or foamed plastic, such as polypropylene, polystyrene or the like and includes a body 20 having a flat upper surface 22 and a recess 24 therein of complex shape. The recess 24 includes a plurality of elongate parallel indentations 26 for receiving a handle 28 of a plurality of conventional toothbrushes 30 having a multiplicity of parallel bristles 32 extending from one end of the handle. The indentations 26 extend in one direction from a larger intermediate or central indentation 34. One or more islands 36 separate the central indentation 34 from a forward indentation 38 where the bristles 32 of the toothbrushes 30 reside.

A plurality of elongate parallel openings 40 extend from adjacent the island 38 toward the end of the base 12 and are separated by a pair of parallel ribs 41. The central indentation 34 extends laterally a greater extent than the indentations 26 to allow the user to retrieve a selected one of the toothbrushes 30 by inserting a finger under the selected toothbrush. It will accordingly be seen that base 12 provides a series of parallel elongate indentations for receiving a plurality of toothbrushes.

The lid 14 is desirably made of the same material as the base 12 and provides a flat surface 42 to abut the surface 22 when the lid 14 is closed. One or more hinges 44 secure the lid 14 to the base 12 for movement between a position closing the top of the base 12 and an open position allowing access to the toothbrushes 30. The toothbrush containing interior of the holder 10 is ventilated through openings 45 in the lid 12 and through openings 46 in the body 20. If the indentations 26, 34, 38 are sufficiently deep to receive the toothbrushes 30 without much margin to accommodate variations in thickness, the surface 42 may be completely planar and without indentations therein. It is more desirable, however, to provide a series of indentations in the bottom of the lid 14 to accommodate the toothbrushes 30.

To this end, the lid 14 provides a large central indentation 47 registering in the lid closed position with the indentation 34, a plurality of end indentations 48 overlying the indentations 26 and an end indentation 50 registering with the indentation 38. A pair of islands 52 register with the islands 36 and a pair of ribs 54 extend forwardly from the islands 52 toward one end of the lid thereby comprising partitions to partially separate and isolate the bristle sections 32 of the toothbrushes 30 in the closed position of the lid.

As shown best in FIG. 2, the bristles 32 of the toothbrushes 30 extend downwardly near the openings 40 to a location near the bottom of the base 12 and are thus exposed to a member 56 including a desiccant material 58 in a recess 60 provided by the closure 16. If desired, the closure 16 may be ventilated to the exterior of the holder 10 to promote evaporation of moisture from the inside thereof. The closure 16 is removably secured to the bottom of the base 12 in any suitable manner, such as by a mortise and tenon connection, VELCRO fasteners 62 or the like. The member 56 includes a permeable cover 57 preferably of a bacteriostatic material by which is meant that the material kills or retards the growth of bacteria. Inside the member 56 is a bottom layer of desiccant material 58 and an upper layer 59 comprising a mass of sorptive material such as fibers for sorbing moisture. It will be seen that the member 56 is readily removed from the closure 16 and is thus preferably disposable.

It is desirable that the toothbrush holder 10 be symmetrical so it will rest flat on an underlying surface and otherwise be aesthetically pleasing. To this end, an odorizer 18 is attached to the base 12 at the opposite end from the closure 16 The odorizer 18 is preferably of mirror image shape to the closure 16 and is removably attached to the bottom of the base 12 in any suitable manner, such as by a sliding mortise and tenon connection or by VELCRO fasteners 66. The odorizer 18 comprises a central recess 68 ventilated to the exterior of the holder 10 through openings 70 which may be of any suitable shape, such as elongate slits. An odorant pad 72 resides in the recess 68 and may be of a conventional type having a bodily flexible permeable cover 74 having a fragrant therein.

It will be seen that the toothbrushes 30 are fairly closely held inside the holder 10 so the holder 10 may be placed in a horizontal, vertical or inclined position without disturbing the toothbrushes 30. Thus, the holder 10 is ideally suited for use either at one's home or while traveling. Typically, the holder 10 is placed horizontally when opening the lid 12.

Use of the toothbrush holder 10 should now be apparent. After use, one of the toothbrushes 30 should be risen and then shaken to remove large water droplets. The toothbrush 30 is placed bristles down in one of the elongate recesses provided by the indentations 26, 34, 38 so the bristles 32 pass through the recess 38 downwardly close to the opening 40. The lid 14 is then closed. Any remaining moisture on the toothbrush 30 drips off onto the member 56 or dries out by evaporation from air circulating through the openings 40, 45, 46. The member 56 dries out due to evaporation through the openings 40 and from contact with the desiccant 58.

Although this invention has been disclosed and described in its preferred forms with a certain degree of particularity, it is understood that the present disclosure of the preferred forms is only by way of example and that numerous changes in the details of construction and operation and in the combination and arrangement of parts may be resorted to without departing from the spirit and scope of the invention as hereinafter claimed.

I claim:

1. A holder for toothbrushes comprising an elongate handle and a multiplicity of parallel bristles extending away from one end of the handle, comprising a base having first and second parallel sides, a plurality of elongate parallel recesses therein open to the first side of the base for receiving a plurality of toothbrushes and a plurality of openings therethrough communicating between the first side and the second side of the base, the handles being receivable in the recesses and the bristles being receivable in the openings;

a lid and means for movably mounting the lid on the base for closing the first side of the base; and a closure for the second side of the base and means for detachably connecting the closure on the base for closing the second side of the base, the closure including a desiccant and a sorptive mass aligned with the openings, the sorptive mass being between the desiccant and the openings.

2. The toothbrush holder of claim 1 wherein the desiccant comprises a container of bodily flexible permeable material having a desiccant material therein.

3. The toothbrush holder of claim 1 wherein the sorptive mass comprises a mass of fibrous material.

4. The toothbrush holder of claim 1 wherein the desiccant comprises a permeable cover of a bacteriostatic material having a desiccant material therein.

5. The toothbrush holder of claim 1 wherein the lid is ventilated.

6. The toothbrush holder of claim 1 further comprising means for emitting an odorant to the exterior of the toothbrush holder including a container having passages therein communicating with the exterior of the holder, means attaching the container to the second side of the base, and an odorant in the container.

7. The toothbrush holder of claim 6 wherein the closure is attached to the second side of the base at a first end thereof and the container is attached to the second side of the base at a second end thereof.

8. The toothbrush holder of claim 1 wherein the base provides at least part of the recesses comprising a first enlarged central indentation, a plurality of second elongate separate parallel indentations extending in one direction away from the central indentation and a third end indentation extending away from the first central indentation in a direction opposite from the second parallel indentations.

9. The toothbrush holder of claim 8 wherein the base provides a plurality of islands dividing the third end indentation into a plurality of separate sections for receiving the one end of the toothbrush.

10. The toothbrush holder of claim 8 wherein the lid provides at least part of the recesses comprising a fourth enlarged central indentation registering with the first central indentation in a closed position of the lid, a plurality of fifth elongate separate parallel indentations extending in one direction away from the fourth central indentation and registering with the second parallel indentations in a closed position of the lid and a sixth end indentation extending away from the fourth central indentation in a direction opposite from the fifth parallel indentations and registering with the third end indentation in a closed position of the lid.

11. The toothbrush holder of claim 10 wherein the lid provides a plurality of islands dividing the sixth end indentation into a plurality of separate sections for receiving the one end of the toothbrush and a partition parallel to the fifth elongate indentations and extending from each of the islands away from the fifth indentations.

* * * * *